(12) United States Patent
Tapalian et al.

(10) Patent No.: US 6,765,211 B2
(45) Date of Patent: Jul. 20, 2004

(54) MICRO-OPTIC ABSORPTION SPECTROMETER

(75) Inventors: Haig Charles Tapalian, Canton, MA (US); Juha-Pekka Laine, Boston, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 303 days.

(21) Appl. No.: 09/896,520

(22) Filed: Jun. 28, 2001

(65) Prior Publication Data

US 2002/0079453 A1 Jun. 27, 2002

Related U.S. Application Data

(60) Provisional application No. 60/214,383, filed on Jun. 28, 2000.

(51) Int. Cl.[7] .............................. G02B 6/12; G02B 6/26
(52) U.S. Cl. ................................. 250/339.07; 385/30
(58) Field of Search ....................... 250/339.07; 385/30, 385/12, 15, 50; 372/18, 74; 436/172; 359/285

(56) References Cited

U.S. PATENT DOCUMENTS

| | | | |
|---|---|---|---|
| 4,695,121 A | | 9/1987 | Mahapatra et al. |
| 4,807,232 A | | 2/1989 | Hart et al. |
| 5,130,843 A | | 7/1992 | He et al. |
| 5,268,693 A | | 12/1993 | Walsh |
| 5,386,126 A | * | 1/1995 | Henderson et al. ............ 257/15 |
| 5,420,688 A | | 5/1995 | Farah |
| 5,436,454 A | * | 7/1995 | Bornstein et al. ...... 250/339.12 |
| 5,742,633 A | | 4/1998 | Stone et al. |
| 5,793,485 A | * | 8/1998 | Gourley ....................... 356/318 |
| 6,009,115 A | | 12/1999 | Ho |
| 6,023,540 A | | 2/2000 | Walt et al. |
| 6,040,191 A | | 3/2000 | Grow |
| 6,058,127 A | | 5/2000 | Joannopoulos et al. |
| 6,266,459 B1 | | 7/2001 | Walt et al. |
| 2002/0071463 A1 | * | 6/2002 | Garnache et al. ............. 372/45 |
| 2002/0172457 A1 | * | 11/2002 | Tapalian et al. .............. 385/30 |

OTHER PUBLICATIONS

Laine, J.P. et al., Silica microsphere resonator and SPARROW waveguide coupler structures, Integrated Photonics Research 2000, OSA Technical Digest, Quebec City, Canada, Jul. 2000.

Laine, J.P. et al., Microsphere resonator mode characterization by pedestal anti-resonant reflecting waveguide coupler, IEEE Photonics Technology Letters, vol. 12, 1004–1006, 2000.

Little, B. et al., Pedestal antiresonant reflecting waveguides for robust coupling to microsphere resonators and for microphotonic circuits, Optics Letters, vol. 25, No. 1, pp. 73–75, 2000.

Laine, J.P. et al., Novel techniques for whispering-gallery-mode excitation in silica microspheres, Integrated Photonics Research 1999, OSA Technical Digest, Santa Barbara, California, Jul. 1999.

* cited by examiner

*Primary Examiner*—Constantine Hannaher
*Assistant Examiner*—Otilia Gabor
(74) *Attorney, Agent, or Firm*—McDermott, Will & Emery

(57) ABSTRACT

An infrared absorption spectrometer features an optical microcavity, and a waveguide that evanescently couples light into the microcavity. The optical resonance frequency of the microcavity is tuned to coincide with an atomic or molecular resonance frequency of a selected atom or molecule. In this way, light coupled into the microcavity will experience absorption in the presence of an atomic or molecular subtance. The absorption causes a measurable change in the evanescent light coupling into the microcavity. The detection sensitivity of the spectrometer is significantly increased, compared to prior art spectrometers, because of the high Q value of the microcavity and the ensuing long optical path lengths of the resonant modes traveling within the microcavity.

23 Claims, 3 Drawing Sheets

MICRO-OPTIC ABSORPTION SPECTROMETER

CROSS-REFERENCE TO RELATED APPLICATIONS

This application claims the benefit of priority from U.S. Provisional Patent Application Serial No. 60/214,383, filed Jun. 28, 2000, entitled Micro-Optic Resonator Readout.

STATEMENT REGARDING FEDERALLY SPONSORED RESEARCH

Not Applicable

REFERENCE TO MICROFICHE APPENDIX

Not Applicable

FIELD OF THE INVENTION

The present invention relates to optical sensors, and in particular to a high-precision, micro-optic absorption spectrometer.

BACKGROUND OF THE INVENTION

During the past few years, a substantial amount of research has been performed in the field of optical microcavity physics, in order to develop high cavity-Q optical microcavity resonators. In general, resonant cavities that can store and recirculate electromagnetic energy at optical frequencies have many useful applications, including high-precision spectroscopy, signal processing, sensing, and filtering. Many difficulties present themselves when conventional planar technology, i.e. etching, is used in order to fabricate high quality optical resonators, because the surfaces must show deviations of less than about a few nanometers. Optical microsphere resonators, on the other hand, can have quality factors that are several orders of magnitude better than typical surface etched optical microresonators, because these microcavities can be shaped by natural surface tension forces during a liquid state fabrication. These microcavities are inexpensive, simple to fabricate, and are compatible with integrated optics.

Optical microcavity resonators have quality factors (Qs) that are higher by several orders of magnitude, as compared to other electromagnetic devices. Measured Qs as large at $10^{10}$ have been reported. The highs resonances encountered in these microcavities are due to whispering-gallery-modes (WGM) that are supported within the microcavities.

As a result of their small size and high cavity Q, interest has recently grown in potential applications of microcavities to fields such as electro-optics, microlaser development, measurement science, and spectroscopy. By making use of these high Q values, microspheric cavities have the potential to provide unprecedented performance in numerous applications. For example, these microspheric cavities may be useful in applications that call for ultra-narrow linewidths, long energy decay times, large energy densities, and fine sensing of environmental changes, to cite just a few examples.

In order for the potential of microcavity-based devices to be realized, it is necessary to couple light selectively and efficiently into the microspheres. Since the ultra-high Q values of microcavities are the result of energy that is tightly bound inside the cavity, optical energy must be coupled in and out of the high Q cavities, without negatively affecting the Q. Further, the stable integration of the microcavities with the input and output light coupling media should be achieved. Also, controlling the excitation of resonant modes within these microcavities is necessary for proper device performance, but presents a challenge for conventional waveguides.

Typically, good overall performance is gained by accessing the evanescent field in a waveguide. Also, only waveguide structures provide easy alignment and discrete, clearly defined ports. Because of cavity and waveguide mode leakage into the substrate and into the modes within the fiber cladding, power extraction from the input optical radiation has proved to be inefficient for conventional planar waveguides, however.

U.S. patent application Ser. No. 09/893,854 (identified by Attorney Docket Nos. CSLL-625 and hereby incorporated by reference) discloses a highly efficient and robust mechanism for coupling optical microcavity whispering-gallery modes into integrated optical waveguide chips. SPARROW (Stripline Pedestal Antiresonant Reflecting Waveguides) are used to achieve vertical confinement and substrate isolation through a highly reflective stack of alternating high and low refractive index dielectric layers. Q-values of over $10^{10}$, and coupling efficiencies of over 98% have been observed.

SPARROW waveguide chips have the potential to integrate optical microcavities into miniaturized optical sensor systems. Because of their ability to excite resonant modes having unprecedentedly high Q-values in optical microcavities, SPARROW waveguide chips have the potential for greatly increasing the resolution and dynamic range in these sensing applications.

In particular, a significant potential application for microcavity resonator devices is chemical/biological agent sensing. Chemical sensors known in the art include MEMS (microelectromechanical systems) chemical sensors, optical waveguide-based sensors, surface plasmon resonance (SPR) chemical sensors, surface acoustic wave (SAW) chemical sensors, mass spectrometers, and IR (infrared) absorption spectrometers Miniaturized sensors, such as prior art MEMS sensors, provide significant advantages. For example, they would be well adapted for in situ functioning. Also, they would be small enough to be deployed in large numbers and implemented for remote probing. It is desirable to provide chemical sensors with an improved resolution, while maintaining the compact size of MEMS sensors known in the art.

SUMMARY OF THE INVENTION

The present invention is directed to a light absorption spectrometer, formed of a waveguide-coupled optical microcavity resonator. The present invention features the tuning of the optical resonance frequency of the microsphere, to coincide with a selected electronic or vibrational transition frequency, so that the light coupled into the microsphere will experience absorption in the presence of an atomic or molecular substance surrounding the microsphere.

An infrared absorption spectrometer constructed in accordance with the present invention includes at least one optical microcavity, and an optical waveguide for coupling light into a resonant mode of the optical microcavity. The optical waveguide has an input end and an output end. The waveguide is adapted for transmitting optical radiation incident on the input end to the output end.

The light coupled into the optical microcavity is adapted to interact with at least one an atomic or molecular species. The atomic or molecular species may be found in a chemical substance surrounding the microcavity, and may be a fluid, by way of example. The optical microcavity is configured so that the frequency of at least one resonant mode of the optical cavity matches an electronic or vibrational transition frequency of the atomic or molecular species. In this way, optical radiation coupled into the optical microcavity and having a frequency substantially equal to the frequency of the resonant mode is absorbed by the atomic or molecular species.

Because of the high Q value and the correspondingly long optical path length of the optical microcavity, the sensitivity of the infrared absorption spectrometer of the present invention is significantly increased, as compared to the prior art.

DETAILED DESCRIPTION

The present invention is directed to an infrared (IR) absorption spectrometer, formed of a waveguide-coupled optical microcavity resonator. Optical microcavities are characterized by high Q values and correspondingly long optical path lengths, allowing a significant increase in the sensitivity of the infrared absorption spectrometer, as compared to prior art absorption spectrometers.

Figure 1:
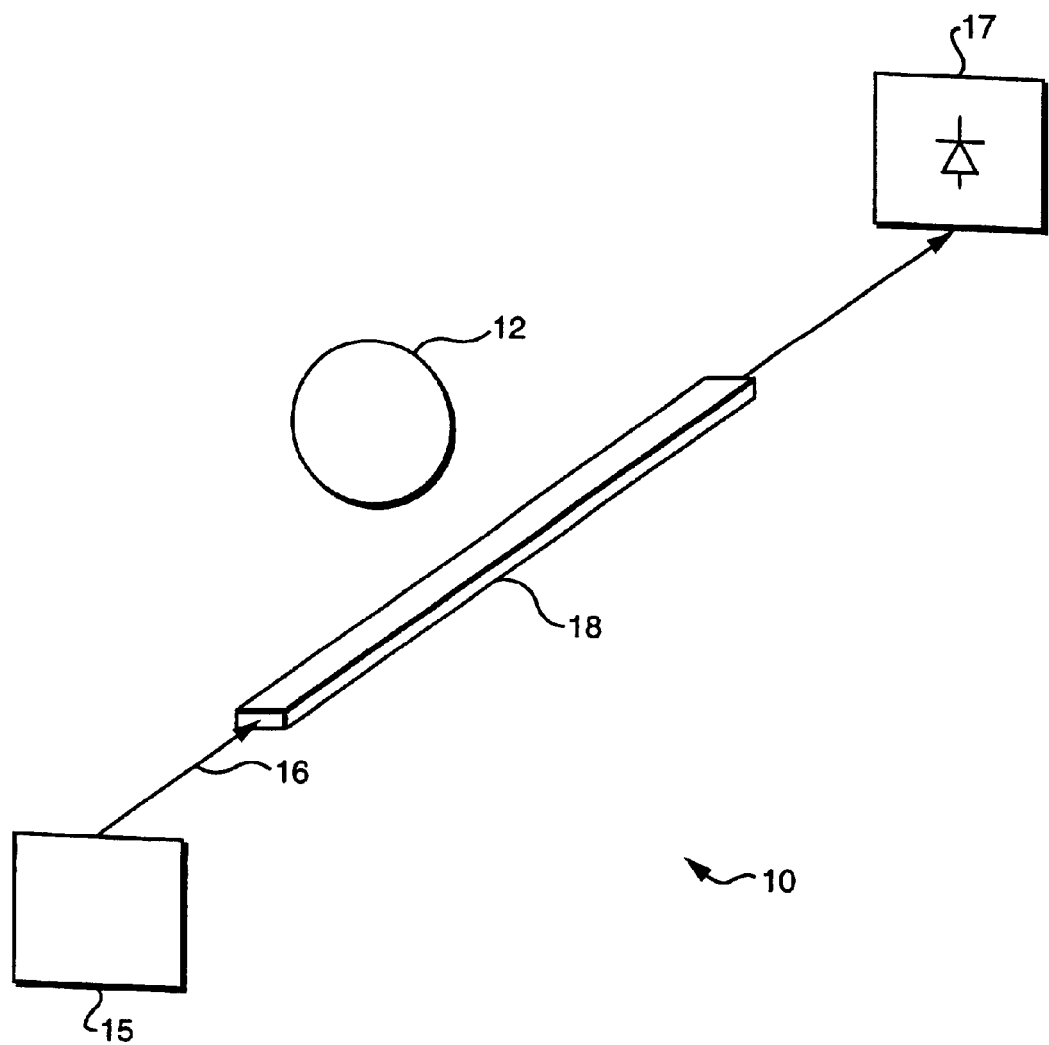
FIG. 1 is a schematic diagram of an infrared absorption spectrometer, constructed in accordance with the present invention.

FIG. 1 is a schematic diagram of an infrared absorption spectrometer 10, constructed in accordance with the present invention. The spectrometer 10 includes at least one optical microcavity resonator 12, and a waveguide 18 for evanescently coupling light from the waveguide 18 onto the microcavity 12. In the present invention, the optical resonance frequency of the microcavity is tuned to coincide with a vibrational resonance frequency of the interacting molecule, such that the light coupled into the microsphere will experience absorption in the presence of the chemical vapor surrounding the microsphere. An optical source 15, preferably a laser, provides a beam 16 of input radiation directed to the waveguide. A photodetector 17 detects optical radiation transmitted through the waveguide 18.

The optical microcavity 12 is a small spherical particle, disk, or ring, having dimensions of the order of microns to millimeters. The optical microcavity 12 is typically made of silica. In a preferred embodiment, the optical microcavity 12 is fabricated by surface tension shaping of the tip of freshly melted optical fiber. Melting of the tip of a silica wire or fiber may be accomplished through arcing in a fusion splicer, by means of a gas flame, or using a high-power laser (such as a $CO_2$ laser) to heat the glass. Microcavities, with diameters typically ranging from about 50 micrometers to about 500 micrometers, are obtained by this method. In the illustrated embodiment, the optical microcavity has a diameter of about 200 micrometers, although other sizes are also within the scope of the present invention.

The optical microcavity 12 is adapted to support WGMs (whispering-gallery-modes), and is thus characterized by extremely high Q values. Light incident on an input end of the waveguide and propagating therethrough is evanescently coupled onto WGM resonances supported within the optical microcavity. An evanescent wave appears whenever a light wave undergoes total internal reflection at a dielectric interface, such as the interface between the silica waveguide and the surrounding air. The evanescent portion of the waveguide mode field is the exponentially decaying portion of the waveguide mode field, outside the relatively high index region of the waveguide. The evanescent wave decays exponentially with the distance from the surface of the waveguide core on a length scale of the order of the optical wavelength.

Evanescent coupling occurs between the waveguide and the microcavity when the wavelength of the evanescent field of the waveguide mode field matches the wavelength of a resonant WGM supported within the microcavity. In a resonant WGM, light is trapped near the surface of the microcavity by repeated total internal reflections, and travels in a circle around the microcavity near the surface of the microcavity. When WGM resonances are excited in the microcavity, light continues to circulate just inside the surface of the microcavity, with virtually no loss except for residual absorption and scattering in the dielectric. This is why extremely high Q-factors, up to over $10^{10}$, can be achieved in the dielectric microcavities constructed in accordance with the present invention. These very high Qs translate into very high optical path lengths, and hence increased sensitivity of the spectrometer.

Figure 2:
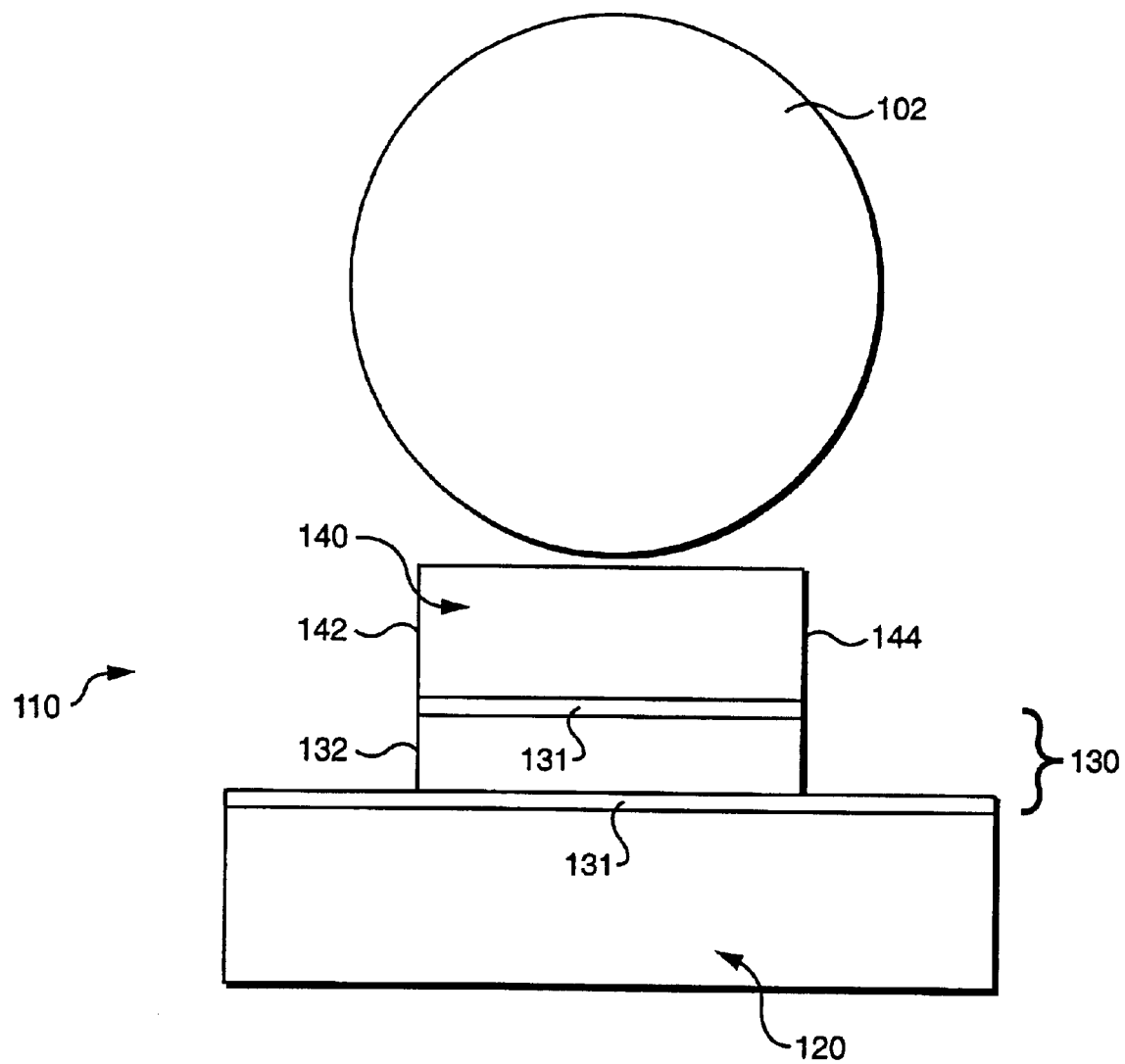
FIG. 2 illustrates a SPARROW optical waveguide, constructed in accordance with the present invention.

In a preferred embodiment, the optical waveguide is a SPARROW (stripline pedestal anti-resonant reflective optical waveguide) waveguide. FIG. 2 illustrates a SPARROW optical waveguide, constructed in accordance with the present invention. The SPARROW waveguide 110 provides an efficient and robust coupling mechanism for exciting whispering-gallery-modes in an optical microcavity 102. The SPARROW 110 includes a multi-layer, high-reflectivity dielectric stack 130 disposed on the substrate 120, and a waveguide core 140. The substrate 120 is substantially planar, and in one embodiment is made of silicon.

The dielectric stack 130 is composed of alternating high ($n_H$) and low ($n_L$) refractive index layers 131 and 132, made of a dielectric material. As a result, the dielectric stack 130 functions as a high reflectivity dielectric mirror. The larger the number of layers 131 and 132, the higher the reflectivity of the stack 130 becomes. While the illustrated embodiment includes only one low index layer 132 disposed between two high index layers 131, the number of the layers 131 and 132 can be increased in order to increase the reflectivity of the stack 130. The alternating layers 131 and 132 forming the dielectric stack 130 provide a cladding for the SPARROW waveguide core 140, i.e. the layers forming the stack 130 may be regarded as cladding layers.

The high reflectivity of the dielectric stack 130 permits isolation of the optical modes of the microcavity 102 and the waveguide core 140 from the waveguide cladding and the substrate. By isolating the waveguide core 140 using the high-reflectivity dielectric stack 130, the SPARROW 110 circumvents the need for obtaining low refractive index cladding materials. As shown in FIG. 2, one of the high refractive index layers 131 is in contact with the substrate 120.

In one embodiment, the high refractive index layer 131 is made of Si (silicon), while the low refractive index layer 132 is made of $SiO_2$ (silica). In one embodiment, the high refractive index $n_H$ is about 3.5, and the low refractive index $n_L$ is about 1.45, although other refractive indices are also within the scope of the present invention. The refractive indices required for efficiently guiding light within the waveguide depend on the wavelength of optical radiation.

The waveguide core 140 is disposed on top of the dielectric stack 130, and is in contact with another one of the high refractive index layers 131. The waveguide core 140 includes an input end 142 and an output end 144, and is adapted for transmitting optical radiation incident on the input end 142 to the output end 144. In one embodiment, the waveguide core is made of silica, and is characterized by the low refractive index $n_L$. In a SPARROW waveguide, the waveguide mode field is essentially entirely contained within the waveguide core 140 on top of the dielectric stack 130, and is isolated from the substrate 120. The successful elimination of both the microcavity mode and the waveguide mode leakage into the substrate results in extremely high coupling efficiencies. Coupling efficiencies approaching 100% have been observed.

Figure 3:
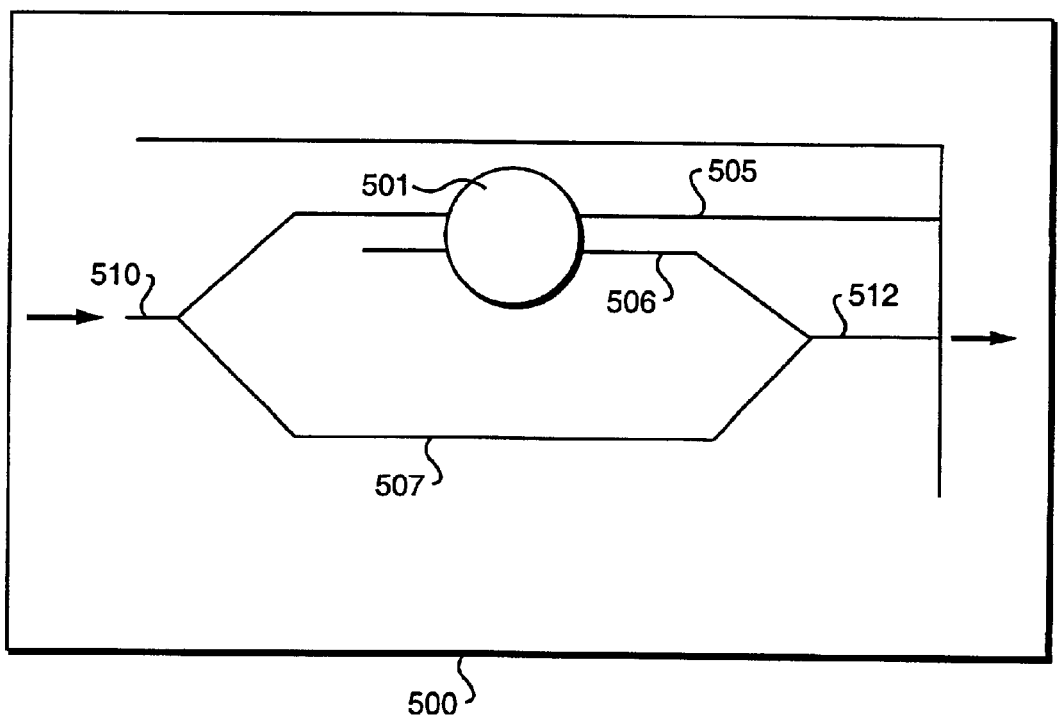
FIG. 3 illustrates an optical waveguide constructed in accordance with the present invention, and having a Mach-Zehnder interferometric configuration.

FIG. 3 illustrates an optical waveguide constructed in accordance with the resent invention, and having a Mach-Zehnder like interferometric configuration. In a Mach-Zehnder interferometer, an incoming optical signal is split into two signals, for example at a Y-junction. Each signal enters a first and a second waveguide branch, respectively. The signals are recombined into an output waveguide, which provides a modulated optical output signal. An electric field applied to one or both of the waveguide branches causes a change in the refractive index in the applied region, corresponding to the changing amplitude of the modulating signal. The change in the index of refraction alters the speed of light in the region, resulting in a change in the delay time of the light passing through the region. The optical path length in one or both of the waveguides branches can be controlled, so that a phase difference results between the two signals when they are recombined at the output waveguide.

The waveguide 500 has an input end 510 and an output end 512. The interferometric waveguide 500 includes three waveguide arms 505, 506, and 507. The first arm 505 forms an input channel, and is adapted to input coupling light into the microsphere. The second arm 506 forms a drop channel, and is adapted to out-couple light from the microcavity into the waveguide. The third arm 507 is used as a reference channel, which has substantially no interaction with the microcavity. At the output end 512, light from the reference channel 507 is combined or interfered with light from the drop channel, i.e. light that has interacted with the microsphere.

The sensitivity of absorption-based sensors is proportional to the optical path length. The change in phase experienced by the resonant light and measured by the interferometer may be expressed in terms of the cavity lifetime τ(d) of the microcavity, and the optical path difference (OPD) τ(d). The cavity lifetime τ(d) for resonant light can be expressed as a function of the total cavity Q:

$$\tau(d) = \frac{Q(d)}{\omega}$$

Assuming interferometer arms of equal path length, the optical path length l(d) can be expressed as a function of the cavity lifetime, $$l(d) = \frac{c}{n}\tau(d) = \frac{\lambda}{2\pi n}Q(d)$$

From the equation provided above, it can be seen that high-Q microcavities provide a way to obtain the high sensitivities associated with long path lengths in a miniature sensor package. In contrast, the optical path lengths available on integrated optical chips are limited, resulting in reduced sensitivity. Using fused silica microcavities as described above, optical path lengths as long as 100 m can be achieved.

In the present invention, the optical resonance frequency of the microsphere is "tuned" to coincide with a selected electronic or vibrational transition frequency such that the light coupled into the microsphere will experience absorption in the presence of an atomic or molecular substance surrounding the microsphere. The result is a change in the measured light transmittance.

The technique of the present invention, when applied to IR absorption spectroscopy, takes advantage of the large absorption coefficients of molecular vibrations in the mid-IR region of the electromagnetic spectrum, typically ranging from about 3 $\mu$M to about 20 $\mu$m. Small molecules, typically 4 atoms or less, possess strong vibrational transitions toward the lower end of the infrared spectrum. The faction of light absorbed by a molecular sample is given by $$I_{a/I0} = 1 - e^{-\alpha \rho L}.$$

here $I_a$ is the absorbed laser intensity,
$I_0$ is the incident laser intensity;
$\alpha$ is the absorption coefficient;
is the vapor pressure of the molecular vapor;
and L is the absorption length, i.e. optical path length.

In one embodiment, the resonant wavelength of fused silica microcavities can be shifted into the mid-infrared region, by coating the microcavities with a gold nanoshell, i.e. a layer of gold having a thickness of the order of nanometers.

In an exemplary embodiment, the infrared absorption technique described above may be implemented using methane, which has a 3.3 $\mu$m vibrational transition. Using an optical microcavity having an optical path length of 50 cm, and an absorption measurement resolution of $10^{-6}$, the methane detection sensitivity is approximately 100 ppt (parts per trillion).

Because of the high-Q values and ensuing large optical path lengths of microcavity resonators, the infrared absorption spectrometer disclosed in the present invention provides a significantly increased sensitivity, as compared to prior art miniature infrared absorption spectrometer. The infrared absorption spectrometer, constructed in accordance with the present invention, provides all the advantages of a compact size, in combination with its high sensitivity. The present invention may have wide ranging applications in the industry and the military, including but not limited to the fields of manufacturing process control, environmental monitoring, combustion bi-product monitoring, and chemical/biological agent sensing on the battlefield.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. An infrared absorption spectrometer, comprising:
    a substrate;
    an optical waveguide having an input end and an output end, said waveguide being adapted for transmitting optical radiation incident on said input end to said output end; and
    at least one optical microcavity constructed and arranged so as to optically interact with light incident on said input end of said optical waveguide, so that light from said waveguide is coupled into said microcavity;
    wherein light coupled into said optical microcavity is adapted to interact with at least one of an atomic and a molecular species; and wherein said optical microcavity is configured so that the frequency of at least one resonant mode of said optical cavity matches a vibrational frequency of said at least one of an atomic and a molecular species, so that optical radiation coupled into said optical microcavity and having a frequency substantially equal to said frequency of said at least one resonant mode is absorbed by said at least one of an atomic and a molecular species.

2. An infrared absorption spectrometer according to claim 1, wherein said optical microcavity is disposed at a distance from said optical waveguide that is sufficiently small to cause an evanescent field of said optical radiation propagating through said optical waveguide to be optically coupled into said microcavity.

3. An infrared absorption spectrometer according to claim 2, wherein said evanescent field is characterized by frequencies substantially equal to a resonant mode of said optical microcavity.

4. An infrared absorption spectrometer according to claim 3, wherein at least one of said resonant modes of said optical microcavity is a whispering gallery mode.

5. An infrared absorption spectrometer according to claim 4, wherein said optical microcavity has a substantially spherical shape, and wherein the wavelengths of the whispering gallery modes of said microcavity are related to the radius r and the degree of sphericity of said substantially spherical microcavity, and are approximately given by the formula:

$$2\pi r = n\lambda,$$

where n is a nonzero integer.

6. An infrared absorption spectrometer according to claim 1, wherein said optical microcavity is selected from the group consisting of microspheres, microdisks, and microrings.

7. An infrared absorption spectrometer according to claim 1, wherein said optical waveguide comprises:
a splitter for splitting said input optical radiation into a first signal and a second signal;
a first waveguide branch and a second waveguide branch for transmitting said first signal and said second signal, respectively; and
a combiner for recombining said first signal and said second signal.

8. An infrared absorption spectrometer according to claim 1, wherein said optical waveguide includes channels arranged in a Mach-Zehnder interferometer configuration.

9. An infrared absorption spectrometer according to claim 1, wherein said optical waveguide includes a drop channel, a throughput channel, and a reference channel, arranged so that the optical microcavity can optically interact with both the drop channel and the throughput channel, but does not substantially optically interact with light in the reference channel.

10. An infrared absorption spectrometer according to claim 1, further comprising a light source arranged to input light into said input end of said optical waveguide.

11. An infrared absorption spectrometer according to claim 1, further comprising at least one detector constructed and arranged so as to detect output optical radiation from said output end of said optical waveguide.

12. An infrared absorption spectrometer according to claim 1, wherein said optical microcavity is made of silica.

13. An infrared absorption spectrometer according to claim 1, wherein said optical waveguide is an integrated optical chip.

14. An infrared absorption spectrometer according to claim 1, wherein the coupling efficiency of said evanescent field of said optical radiation coupled into said optical microcavity is from about 10% to about 98%.

15. An infrared absorption spectrometer according to claim 1, wherein said optical microcavity is fabricated by melting one end of an optical fiber.

16. An infrared absorption spectrometer according to claim 1, wherein said optical microcavity is characterized by a quality factor (Q) from about $10^5$ to about $10_{10}$.

17. An infrared absorption spectrometer according to claim 1, wherein said optical microcavity is characterized by a diameter of about 50 µm to about 500 µm.

18. An infrared absorption spectrometer according to claim 1, wherein said optical microcavity is characterized by a diameter of about 200 µm.

19. An infrared absorption spectrometer according to claim 2, wherein said distance is less than one wavelength of said optical radiation propagating through said optical waveguide.

20. An infrared absorption spectrometer according to claim 1, wherein said optical waveguide comprises:
(a) a multi-layer dielectric stack disposed on said substrate, said dielectric stack including alternating high and low refractive index dielectric layers; and
(b) a waveguide core disposed on said dielectric stack and having an input end and an output end, said waveguide core being adapted for transmitting optical radiation incident on said input end to said output end.

21. An infrared absorption spectrometer according to claim 20, wherein one of said low refractive index layers is in contact with said substrate, and wherein one of said high refractive index layers is in contact with said waveguide core.

22. An infrared absorption spectrometer according to claim 20, wherein said low index dielectric layer and said waveguide core comprises silica.

23. An infrared absorption spectrometer according to claim 20, wherein said high index dielectric layer comprises silicon.

* * * * *

UNITED STATES PATENT AND TRADEMARK OFFICE
CERTIFICATE OF CORRECTION

PATENT NO.     : 6,765,211 B2
DATED          : July 20, 2004
INVENTOR(S)    : Haig Charles Tapalian et al.

It is certified that error appears in the above-identified patent and that said Letters Patent is hereby corrected as shown below:

Column 8,
Line 22, after "from $10^5$ to about" delete "$10_{10}$" and insert thereof -- $10^{10}$ --.

Signed and Sealed this

Seventh Day of December, 2004

JON W. DUDAS
*Director of the United States Patent and Trademark Office*